US009463008B2

(12) United States Patent
Thal

(10) Patent No.: US 9,463,008 B2
(45) Date of Patent: Oct. 11, 2016

(54) MULTI-LOOP ADJUSTABLE KNOTLESS ANCHOR ASSEMBLY, ADJUSTABLE CAPTURE MECHANISM, AND METHOD FOR REPAIR

(76) Inventor: Raymond Thal, McLean, VA (US)

( * ) Notice: Subject to any disclaimer, the term of this patent is extended or adjusted under 35 U.S.C. 154(b) by 20 days.

(21) Appl. No.: 13/472,772

(22) Filed: May 16, 2012

(65) Prior Publication Data

US 2012/0296375 A1 Nov. 22, 2012

Related U.S. Application Data

(60) Provisional application No. 61/486,570, filed on May 16, 2011, provisional application No. 61/500,655, filed on Jun. 24, 2011.

(51) Int. Cl.
*A61B 17/04* (2006.01)

(52) U.S. Cl.
CPC .... *A61B 17/0401* (2013.01); *A61B 2017/0403* (2013.01); *A61B 2017/044* (2013.01); *A61B 2017/0414* (2013.01); *A61B 2017/0427* (2013.01); *A61B 2017/0445* (2013.01); *A61B 2017/0448* (2013.01); *A61B 2017/0453* (2013.01); *A61B 2017/0458* (2013.01); *A61B 2017/0475* (2013.01)

(58) Field of Classification Search
CPC .......... A61B 17/0401; A61B 17/0469; A61B 17/0487; A61B 17/06166; A61B 2017/0414; A61B 2017/0427; A61B 2017/0445; A61B 2017/0448; A61F 2/0811
USPC ........................................ 606/228, 232, 148
See application file for complete search history.

(56) References Cited

U.S. PATENT DOCUMENTS

| | | | |
|---|---|---|---|
| 5,569,306 A * | 10/1996 | Thal | 606/232 |
| 5,782,864 A * | 7/1998 | Lizardi | 606/232 |
| 5,891,168 A | 4/1999 | Thal | |
| 6,024,758 A * | 2/2000 | Thal | 606/232 |
| 6,319,271 B1 * | 11/2001 | Schwartz et al. | 606/232 |
| 8,814,905 B2 * | 8/2014 | Sengun | A61B 17/0401 289/1.5 |
| 2005/0187577 A1* | 8/2005 | Selvitelli et al. | 606/232 |
| 2006/0079904 A1 | 4/2006 | Thal | |
| 2006/0190042 A1 | 8/2006 | Stone et al. | |
| 2007/0083236 A1 | 4/2007 | Sikora et al. | |
| 2009/0082805 A1 | 3/2009 | Kaiser et al. | |
| 2010/0094425 A1 | 4/2010 | Bentley et al. | |
| 2012/0165864 A1* | 6/2012 | Hernandez et al. | 606/232 |

OTHER PUBLICATIONS

Alberta, Frank G. et al., "Arthroscopic Knot Tying", Textbook of Arthroscopy, vol. 355, Miller, MD, Col, BJ (eds), 2004, Chapter 4, 29-38.
Lo, Ian K.Y. et al., "Arthroscopic Knots: Determining the Optimal Balance of Loop Security and Knot Security", Arthroscopy: The Journal of Arthroscopic and Related Surgery, Vo.
McMillan, Eric R and Richard B Caspari, "7 Arthroscopic Knot-Tying Techniques", An Atlas of Shoulder Arthroscopy, Imhoff AB, Ticker JB, Fu FH (eds). London: Martin Dunitz, 200.

* cited by examiner

*Primary Examiner* — Julie A Szpira
(74) *Attorney, Agent, or Firm* — Welsh Flaxman & Gitler LLC

(57) ABSTRACT

A suture anchoring system includes a mounting sleeve having an open distal end and an open proximal end defining a passageway therethrough. The system also includes a first elongated member with an anchor suture secured thereto and a tissue suture loop. A method for securing tissue includes passing a tissue suture loop through the tissue such that opposed first and second loop sections are formed, passing an anchor suture through first and second openings respectively defined by the opposed first and second loop sections, capturing the anchor suture after passing through the first and second openings with a first elongated member attached to the anchor suture, and securing the first elongated member attached to the anchor suture to a desired anchor hole in an anatomical site.

6 Claims, 17 Drawing Sheets

MULTI-LOOP ADJUSTABLE KNOTLESS ANCHOR ASSEMBLY, ADJUSTABLE CAPTURE MECHANISM, AND METHOD FOR REPAIR

CROSS REFERENCE TO RELATED APPLICATION

This application claims the benefit of U.S. Provisional Patent Application Ser. No. 61/486,570, entitled "MULTI-LOOP ADJUSTABLE KNOTLESS ANCHOR ASSEMBLY AND METHOD FOR REPAIR", filed May 16, 2011, and U.S. Provisional Patent Application Ser. No. 61/500,655, entitled "MULTI-LOOP ADJUSTABLE KNOTLESS ANCHOR ASSEMBLY AND METHOD FOR REPAIR", filed Jun. 24, 2011,

BACKGROUND OF THE INVENTION

1. Field of the Invention

The present invention relates to devices or methods used in tissue repair, more particularly, devices and methods for attachment of biological tissue (i.e., tendons or ligaments) to a bone mass.

2. Description of the Related Art

Soft tissues, such as tendons and ligaments, generally are attached to bone by small collageaous fibers. These connections are strong but permit the tendons and ligaments to be flexible. When a tissue, or a portion of a tissue, is torn away from the bone and requires repair, a surgeon is often required to repair the detached soft tissue with sutures, which are passed through bone tunnels and tied. A number of devices have been developed for securing a ligament or tendon to a bone mass. These devices can be used in place of bone tunneling techniques. These attachment devices are usually anchor element through extensive surgical incisions and, in some circumstances, by arthroscopic surgical techniques. The placement of bone tunnels for repair can be difficult and generally require large open incisions. Recently, through the advent of arthroscopic surgery, where the surgeon looks into a joint cavity with an arthroscope, there has been a trend to repair soft tissues back to bone through small incisions called portals. The unique free loop knotless suture anchor assemblies described herein facilitate this difficult and precise procedure.

A variety of devices are available for attaching objects to bone, such as screws, staples, cement, suture anchors, and sutures alone. These devices have been used to attach soft tissue, such as ligaments, tendons, muscles, as well as objects such as prostheses, to bone. A suture anchor assembly is a device, which utilizes small anchors with suture materials attached thereto. A device, such as a screw, is inserted into the bone mass and anchored in place. After insertion of the anchor, the attached suture is passed through the tissue to be repaired. The tying of a knot in the suture is then required to secure the tissue to the bone. The process of passing the anchored suture through the soft tissue and tying a knot is time consuming and difficult to undertake in the tight space encountered during arthroscopic surgery and sometimes even in conventional open surgery.

Knotless anchor assemblies have been popular and are embodied in a number of prior patents such as U.S. Pat. No. 6,045,574 wherein there is provided an assembly with an anchor means having a snag means, and a hollow sleeve element with a loop suture element attached thereto, wherein the snag means captures a loop suture element of the hollow sleeve element to draw tissue into secure attachment with a bone mass.

However, difficulties still exist and the present invention attempts to address these with a method and apparatus for knotless suture anchoring.

SUMMARY OF THE INVENTION

It is, therefore, an object of the present invention to provide a suture anchoring system including a first anchor with an anchor suture loop secured thereto and a tissue suture loop.

It is also an object of the present invention to provide a suture anchoring system wherein the tissue suture loop includes a one-way sliding, locking knot with a tensioning suture component extending therefrom.

It is another object of the present invention to provide a suture anchoring system wherein the anchor suture loop includes a one-way sliding, locking knot with a tensioning suture component extending therefrom.

It is a further object of the present invention to provide a suture anchoring system wherein the first anchor is an elongated member having a first end and a second end, the first end including a first aperture and the second end includes a second aperture.

It is also an object of the present invention to provide a suture anchoring system wherein the anchor suture loop is secured to a first end of the first anchor and a second end of the first anchor includes a snag member shaped and dimensioned for engaging a free end of the anchor suture loop.

It is another object of the present invention to provide a suture anchoring system including a sleeve shaped and dimensioned for receiving the first anchor.

It is a further object of the present invention to provide a suture anchoring system wherein the first anchor includes an external surface with means for engaging with a recess of the sleeve.

It is also an object of the present invention to provide a suture anchoring system including a mounting sleeve having an open distal end and an open proximal end defining a passageway therethrough, a first elongated member with an anchor suture secured thereto, and a tissue suture loop.

It is another object of the present invention to provide a suture anchoring system including a second elongated member secured to the anchor suture.

It is a further object of the present invention to provide a method for securing tissue including passing a tissue suture loop through the tissue such that opposed first and second loop sections are formed, passing an anchor suture through first and second openings respectively defined by the opposed first and second loop sections, capturing the anchor suture after passing through the first and second openings with a first elongated member attached to the anchor suture, and securing the first elongated member attached to the anchor suture to a desired anchor hole in an anatomical site.

It is also an object of the present invention to provide a method for securing tissue wherein the anatomical site is a bone surface.

It is another object of the present invention to provide a method for securing tissue wherein a first end of the anchor suture is secured to the first elongated member and a second end of the anchor suture is secured to a second elongated member, and the first and second elongated members are secured with in a mounting sleeve at an anchor hole at the anatomical site.

It is a further object of the present invention to provide a method for securing tissue wherein the mounting sleeve includes an open proximal end and an open distal end defining a cylindrical passageway and allowing access therethrough. The method further includes the step of passing both the first and second elongated members through the passageway and into the small cavity defined by a bottom of the anchor hole, and orienting the first and second anchors transversely to a longitudinal axis of the cylindrical mounting sleeve to thereby lock the first and second elongated members in position.

It is also an object of the present invention to provide a method for securing tissue wherein a first end of the anchor suture is secured to first end of the first elongated member and a free end of the anchor suture is captured by a snag member of the first elongated member prior to securing the first elongated member.

It is another object of the present invention to provide a method for securing tissue further including the step of tensioning either the tissue suture loop or the anchor suture.

It is a further object of the present invention to provide a method for securing tissue further including the step of tensioning the tissue suture loop.

It is also an object of the present invention to provide a method for securing tissue wherein the anchor suture is an anchor suture loop and the method includes the further step of tensioning the anchor suture loop.

It is another object of the present invention to provide a method for securing tissue further including a cylindrical anchor mounting sleeve shaped and dimensioned for receiving the first elongated member, the cylindrical anchor mounting sleeve includes an open proximal end and an open distal end defining a passageway and allowing access therethrough, wherein the cylindrical anchor mounting sleeve is positioned within the anatomical site.

It is a further object of the present invention to provide a method for securing tissue further including the step of passing the first elongated member through the passageway and into the small cavity defined by a bottom of the anchor hole, and orienting the first anchor transversely to a longitudinal axis of the cylindrical anchor mounting sleeve to thereby lock the bone anchor in position.

Other objects and advantages of the present invention will become apparent from the following detailed description when viewed in conjunction with the accompanying drawings, which set forth certain embodiments of the invention.

DESCRIPTION OF THE PREFERRED EMBODIMENTS

Figure 1:
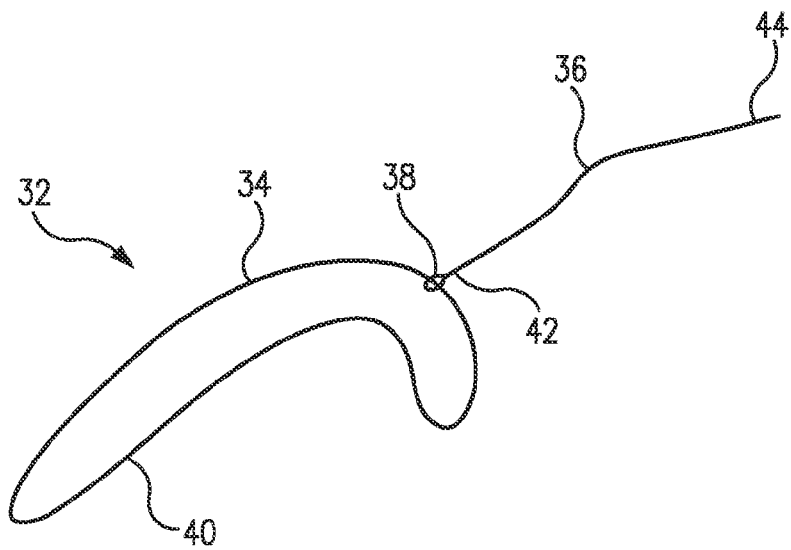
FIG. 1 is a perspective view of the adjustable suture loop.

The detailed embodiments of the present invention are disclosed herein. It should be understood, however, that the disclosed embodiments are merely exemplary of the invention, which may be embodied in various forms. Therefore, the details disclosed herein are not to be interpreted as limiting, but merely as a basis for teaching one skilled in the art how to make and/or use the invention.

In accordance with the present invention, and with reference to FIGS. 1 to 6, the present procedure is achieved using existing bone anchors 1, for example, the BIOKNOTLESS™/LUPINE™ bone anchors of DePuy Mitek as described in U.S. Pat. Nos. 5,709,708 and 5,782,864, which are incorporated by reference, and which are shown in FIGS. 2, 4, 5 and 6.

Each of the bone anchors 1 preferably employed in accordance with the present invention is composed of an anchor member 10 having a first end 20 and a second end 22. A suture element in the form of an anchor suture loop 12 is provided and can be fixedly secured at the first end 20 and/or the second end 22 of the anchor member 10 such that the anchor suture loop 12 includes a fixed end 24 directly secured at the first end 20 of the anchor member 10 and a free end 26 that may be freely manipulated in accordance with the present invention. Conversely, the anchor suture loop may be attached to any desired location on the anchor member or separate and free from the anchor member. It is also appreciated, the anchor suture loop can be secured by a knot or just passed through the aperture 52. Also, the anchor suture loop 12 can be attached with a sliding, locking knot that allows adjustability to the size of loop 12, which can be used to tension the repair. In accordance with a preferred embodiment, the anchor suture loop 12 is retained in an aperture 52 formed adjacent the first end 20 of the anchor member 10, although it is appreciated other attachment arrangements and mechanisms may be employed.

The second end 22 of the anchor member 10 includes a snag member 14 shaped and dimensioned for engaging the free end 26 of the anchor suture loop 12. In accordance with a preferred embodiment, the snag member 14 is a notch formed in the second end 22 of the anchor member 10. Although the embodiment disclosed herein employs a snag member in the form of a notch at the second end of the anchor member, it is appreciated other snag member structures and positions may be employed as shown in U.S. Pat. Nos. 5,709,708 and 5,782,864.

The anchor member 10 also includes, if desired, lateral extending prongs 16, 18 shaped and dimensioned to facilitate the attachment of the anchor member 10 to a bone mass 28. The anchor member 10 is also provided with a selectively detachable deployment arm 50 that is used in the manipulation of the anchor member 10 as it is deployed as discussed below in greater detail. It is appreciated the bone anchor 1 can also contain, or be configured with, umbrella spokes, it can contain threads, be expandable, or have any other type of engaging features on its exterior for secure attachment with a bone mass. All of these exterior attachment features are known to the industry and may be readily applied to the bone anchor of the present invention.

Briefly, the present invention achieves secure, tensioned attachment of soft tissue 30 to a bone mass 28 using a bone anchor 1 as described above in conjunction with an adjustable suture loop 32 composed of loop member 34 with a tensioning suture component 36 extending therefrom and coupled thereto through the creation of a slip (or sliding) knot 38. The adjustable suture loop 32 is preferably flexible and/or inelastic, and may be prepared with a pre-tied sliding knot. The free end of the adjustable suture loop 32, that is, the second end 44 of the tensioning suture component 36, is left in place to allow for additional tensioning as is discussed below in greater detail. It is appreciated, the tensioning suture component, as shown in FIG. 1, can be composed of more than one suture and may have multiple free ends.

The adjustable suture loop 32 is composed of one or more strands of suture 40. The adjustable suture loop 32 includes a first segment and a second segment tied so as to form a loop member 34 and one or more tensioning suture components 36 extending from the loop member 34. As such, the tensioning suture component 36, as shown in FIG. 1, may be composed of more than one suture depending upon the number of strands of suture used in the construction of the adjustable suture loop. The tensioning suture component 36 includes a first end 42 and a second end 44. The first end 42 is secured to the loop member 34 at the sliding, locking knot 38 defining the loop member 34, while the second end 44 freely extends therefrom for manipulation by the medical practitioner as discussed below in greater detail.

The adjustable suture loop 32 is constructed by tying the first segment and the second segment of the strand of suture 40 with a sliding, locking knot 38. As is appreciated, various knot types and a sliding, locking knot is formed in the manner disclosed in Arthroscopic Knot Tying, Frank G. Alberta, et al. (Arthroscopic Knot Tying Chapter 4: pp. 29-38); Arthroscopic knot-tying techniques, Eric R McMillan et al. (An Atlas of Shoulder Arthroscopy Imhoff AB Tucker IB Eu EH (eds) pp 81-95); and Arthroscopic Knots: Determining the Optimal Balance of Loop Security and Knot Security, Ian K. Y. Lo, et al. (The Journal of Arthroscopic and Related Surgery, Vol 20, No 5 (May-June). 2004: pp. 489-502). By constructing the adjustable flexible suture loop 32 with a sliding, locking knot 38, one can alter the size of the loop member 34 by pulling upon the tensioning suture component 36, which functions by pulling a portion of the suture strand 40 through the sliding, locking knot 38 and ultimately reducing the size of the loop member 34 while increasing the length of the tensioning suture component 36.

Figure 2:
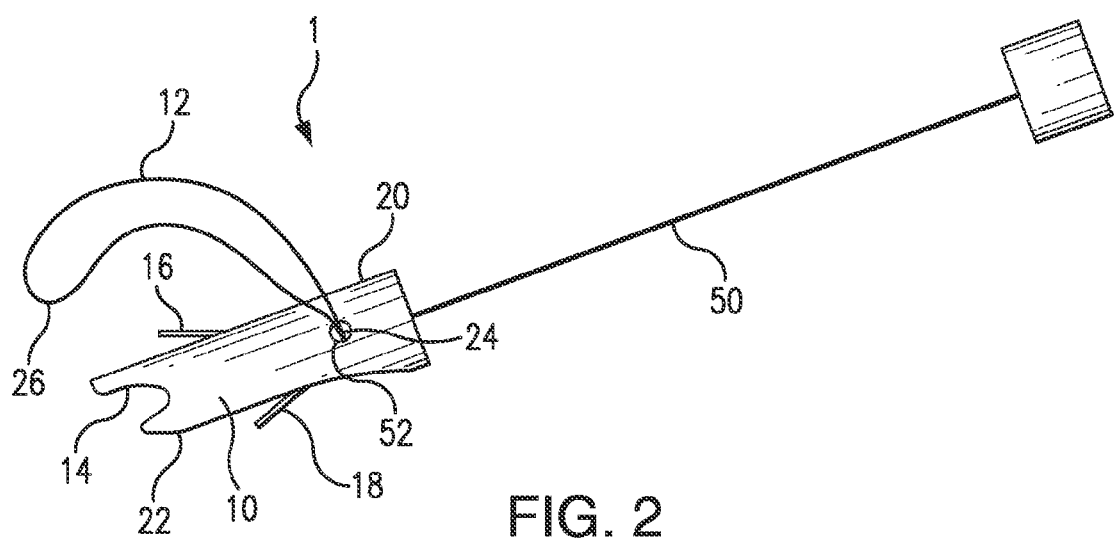
FIG. 2 is a perspective view of the bone anchor.
Figure 3:
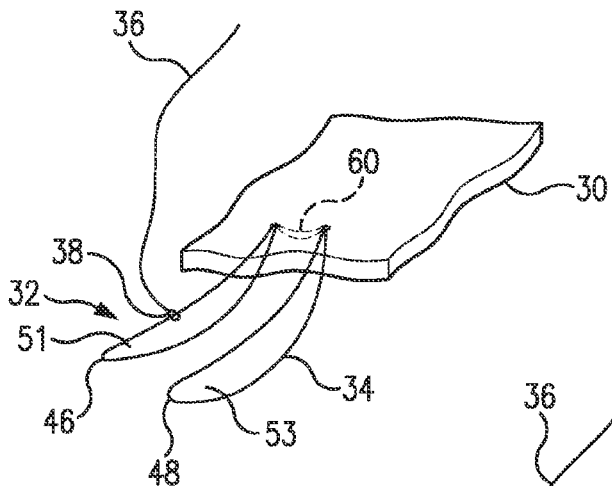
FIGS. 3, 4 and 5 show the steps of the present method.
Figure 4:
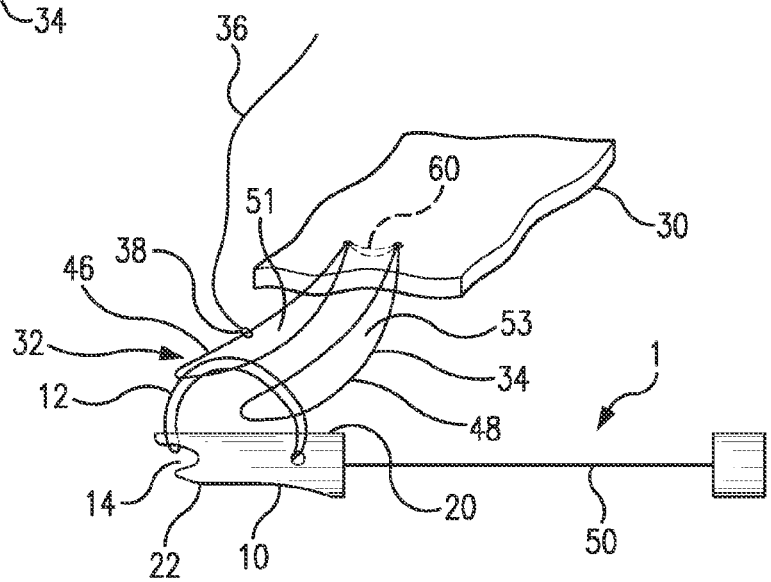

In accordance with the present method, the adjustable suture loop 32 is first passed through the soft tissue 30 one wishes to secure to a bone mass 28. Referring to FIG. 3, the adjustable suture loop 32, in particular, the loop member 34 thereof is drawn through the soft tissue 30 with a surgical needle. A variety of suture passing methods can be used such as arthroscopic suture passers, arthroscopic suture shuttling devices or suture, or the like. The loop member 34 is passed through the soft tissue 30, one or more times, such that opposed first and second loop sections 46, 48 are formed when the loop member 34 is effectively split into two sections by the soft tissue 30; that is, with the soft tissue 30 between the opposed loop sections 46, 48. In particular, the loop member 34 is pulled through the soft tissue 30 until the two loop sections 46, 48 are of substantially the same size and in alignment. Pulling of the loop member 34 through the tissue is preferably achieved using a "utility suture" in a manner known to those skilled in the art. It is appreciated the loop member 34 is relatively long so that the opposed loop sections 46, 48 may be brought outside of the joint under repair. As shown in FIGS. 2, 3 and 4, the tensioning suture component 36 of the adjustable suture loop 32 also extends from one of the loop sections 46 and is similarly accessible from outside of the joint under repair.

With the loop sections 46, 48 of the adjustable suture loop 32 outside of the joint, and with reference to FIG. 4, the anchor suture loop 12 of the anchor member 10 is passed through the openings 51, 53 respectively defined by the opposed first and second loop sections 46, 48. That is, the free end 26 of the anchor suture loop 12 is drawn through the openings 51, 53 such that the anchor suture loop 12 is intertwined or linked with the opposed loop section 46, 48. In this arrangement, the central portion 60 of the loop member 34 between the loop sections 46, 48 is in direct contact with the soft tissue 30 securing the anchor suture loop 12 to the soft tissue 30 such that the loop sections 46, 48 may simultaneously pull against the anchor suture loop 12 without fear that the loop member 34 will become disengaged with the soft tissue 30.

Thereafter, the free end 26 of the anchor suture loop 12 is captured by the snag member 14 of the anchor member 10; that is, the free end 26 of the anchor suture loop 12 is captured, entangled, coupled to, or otherwise attached to the snag member 14 at the second end 22 of the anchor member 10 for manipulation of the anchor suture loop 12 and ultimately fixed attachment of the free end 26 of the anchor suture loop 12 to the snag member 14 at the second end 22 of the anchor member 10 upon deployment of the bone anchor 1 within the bone mass 28 to which the soft tissue 30 is secured. It is appreciated that if the snag member is not positioned at the second end of the anchor, which is possible as discussed above, the free end of the anchor suture loop would be fixed wherever the snag member is located.

Figure 5:
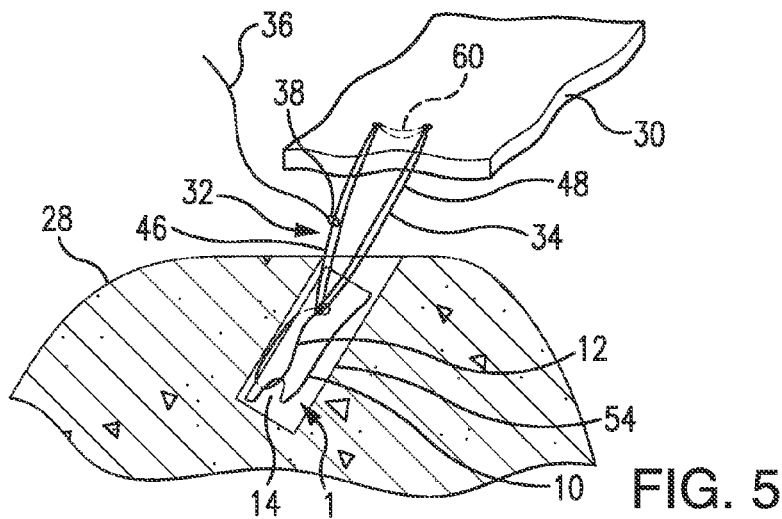

With the anchor suture loop 12 passed through the openings 51, 53 defined by the opposed first and second loop sections 46, 48 and the free end 26 of the anchor suture loop 12 captured by the snag member 14 at the second end 22 of the anchor member 10, the anchor suture loop 12 is linked to the loop member 34 and ultimately the soft tissue 30. Referring to FIG. 5, the bone anchor 1 is then inserted within an anchor hole 54 preferably predrilled in the bone mass 28. It is appreciated, the anchor member 10 can also be pushed into or screwed into the bone mass 28, if desired. In accordance with the disclosed embodiment, the bone anchor 1 is inserted into the hole 50 securing the two ends of the suture in the bone mass 28. It is appreciated; the bone anchor can be deployed by toggling, flipping, or the like. Alternatively, the anchor member may have a second hole or opening on its second end, and the suture loop is wrapped around the tip of the anchor member. It is also appreciated, a mounting sleeve may be inserted into the anchor hole and the anchor member secured directly to the mounting sleeve instead of the anchor hole. After the anchor member is passed in the hole or in a threaded anchor mounting sleeve, if desired, the anchor member can be rotated so it locks in place on the end of the anchor mounting sleeve. The provision of the sliding, locking knot on anchor suture loop allows for adjustment in the size of this loop. This adjustability is useful in several aspects of the surgical procedure.

Figure 6:
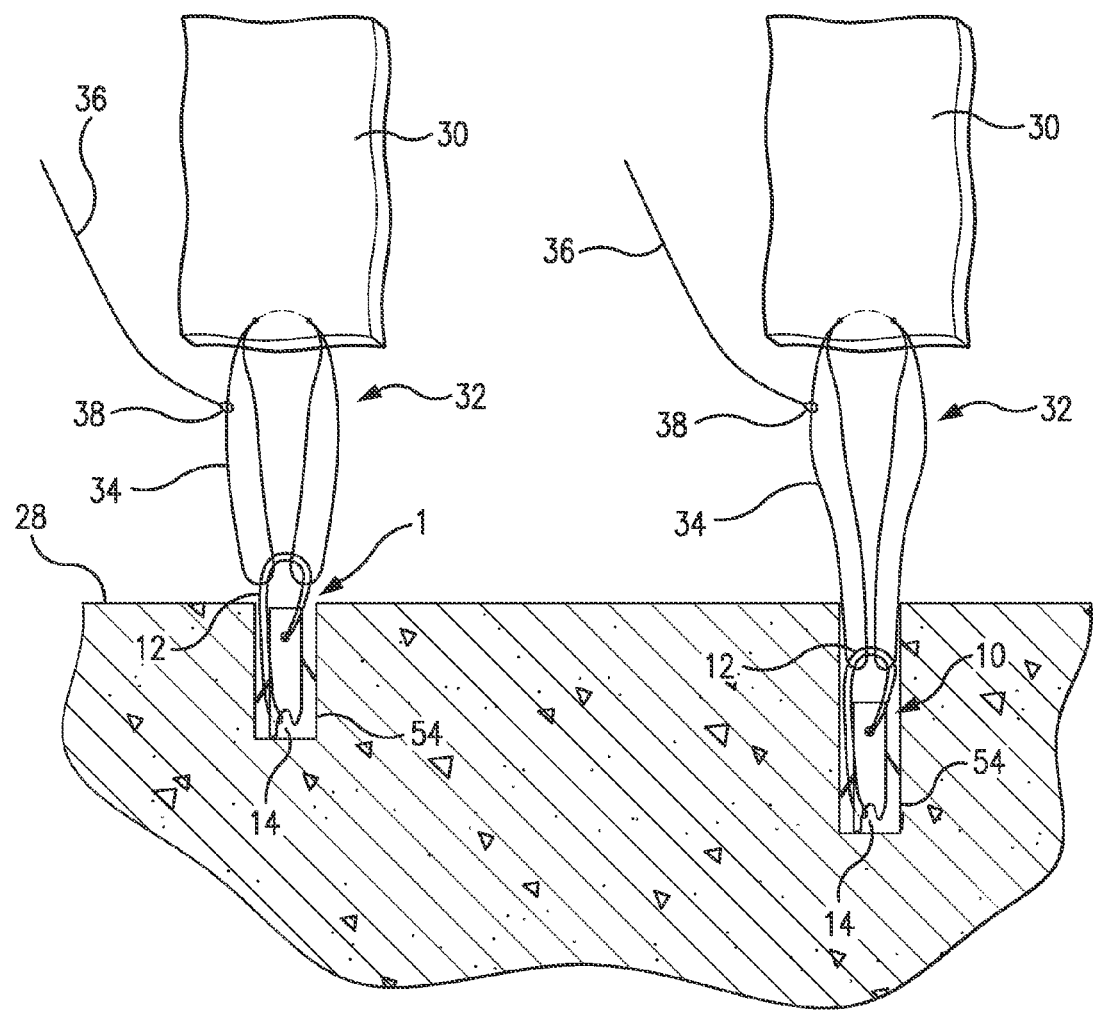
FIG. 6 shows bone anchors deployed at different depths within a bone mass in accordance with the present invention.
Figure 7:
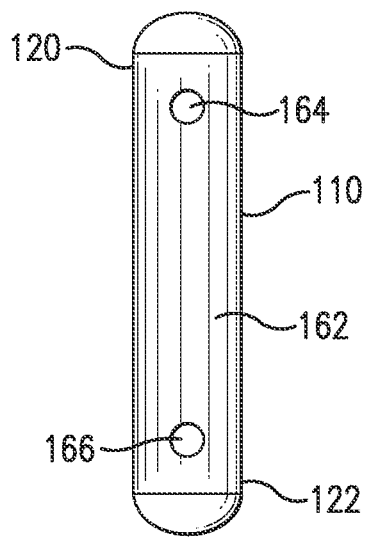
FIGS. 7, 8 and 9 are respectively a front plan view, a side plan view and a perspective view of an anchor member in accordance with an alternate embodiment.
Figure 8:
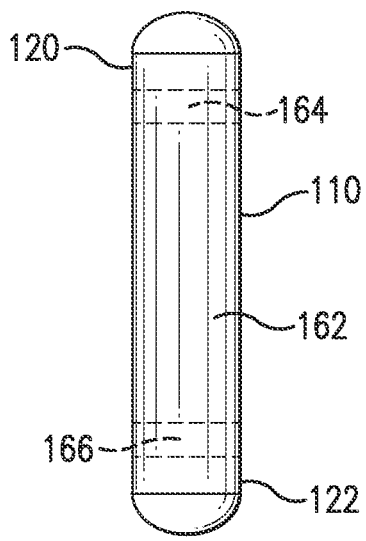
Figure 9:
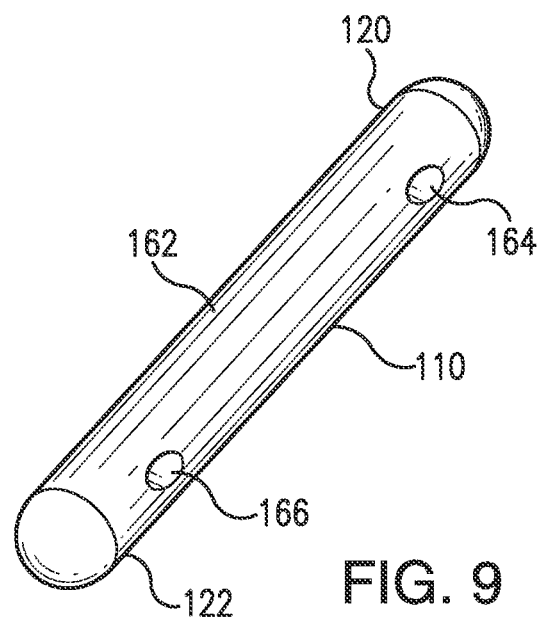

With the bone anchor 1 securely held within the drill hole 54, the loop member 34 is tensioned so as to reduce the size of the loop member 34 and draw the soft tissue toward the bone mass 28. In particular, the tensioning suture component 36 is pulled in a direction away from the loop member 34 causing the suture strand 40 to be drawn through the sliding, locking knot 38 reducing the size of the loop member 34 and consequently drawing the soft tissue 30 toward the bone mass 28 since the size of the anchor suture loop 12 is fixed. The tensioning suture 36 is pulled and the loop member 34 size is reduced until such a time that the soft tissue 30 is fully pulled toward the bone mass 28. The procedure may be repeated depending upon the needs of the procedure. The excess suture material of the tensioning suture component(s) 36 may then be cut away and the incision closed. With some anchor member designs, additional tensioning can be achieved by pushing the anchor deeper into the drill hole after the loop is tensioned by the sliding, locking knot. Referring to FIG. 6, it is also appreciated the present invention allows for anchoring and soft tissue attachment with limited regard for the depth of the drilled hole or the depth of the bone anchor within the bone mass. This results from ability to draw the soft tissue 30 toward the bone anchor 1 and bone mass 28 under the control of the adjustable suture loop 32, in particular pulling of the tensioning suture component 36 which results in a reduction in the size of the loop member 34. Because the size of the loop member 34 dictates how far the soft tissue 30 is pulled toward the bone mass 28/bone anchor 1, a medical practitioner can readily control the position of the soft tissue 30 relative to the bone mass 28/bone anchor 1.

As briefly discussed above, it is appreciated other bone anchor structures may be employed in accordance with the present invention. Such a bone anchor is disclosed with reference to FIGS. 7 to 14, and is used in conjunction with the adjustable suture loop described above.

The bone anchor 100 is composed of an anchor member 110 having a first end 120 and a second end 122. A suture element 112, in the form of an anchor suture loop is provided and can be fixedly secured at the anchor member 110 as discussed below in greater detail.

The anchor member 110 includes an elongated body 162. In accordance with a preferred embodiment, the elongated body 162 is preferably, cylindrical shaped, and includes a rounded first end 120 and a rounded second end 122. The elongated body 162 includes spaced first and second apertures 164, 166. The first and second apertures 164, 166 are preferably positioned adjacent the first end 120 and the second end 122 of the elongated body 162, respectively. It is, however, appreciated other aperture positions are possible.

As with the prior embodiment, the anchor member 110 may also include, if desired, lateral extending prongs shaped and dimensioned to facilitate the attachment of the anchor member 110 to a bone mass 128. The anchor member 110 is also provided with a selectively detachable deployment arm 150 that is used in the manipulation of the anchor member 110 as it is deployed as discussed below in greater detail.

The anchor suture loop 112 is coupled to the anchor member 110 by controlled entanglement with the first and second apertures 164, 166 and the elongated body 162 of the anchor member 110. For example, and in conjunction with a first manner of attachment, the anchor suture loop 112 is fixedly secured at the first aperture 164 in a manner similar to the embodiment disclosed with reference to FIGS. 1 to 6. Considering such an attachment mechanism, the anchor suture loop 112 may be thought of as including a fixed (or first) end 124 directly secured at the first aperture 164 of the anchor member 110 and a free (or second) end 126 that may be freely manipulated for passage through the second aperture 166. When it is desired to entangle the anchor suture loop 112 with the adjustable suture loop 132, the free end 126 of the anchor suture loop 112 is passed through the second aperture 166 creating an entanglement loop 170 at the second aperture 166 opposite the entry point for the free end 126 of the anchor suture loop 112, as well as an engagement loop 172 between the first aperture 164 and the second aperture 166. The entanglement loop 170 is then looped around the elongated body 162 adjacent the second end 122 of the anchor member 110 effectively locking the anchor suture loop 112 in position when tension is applied to the engagement loop 172 formed by the anchor suture loop 112 between the first aperture 164 and the second aperture 166.

In accordance with an alternate attachment mechanism, the anchor suture loop 112' may be initially separate from the anchor member 110' and secured thereto by looping the anchor suture loop 112' over the elongated body 162' at both the first end 120' and the second end 122' of the anchor member 110'. Considering the anchor suture loop 112' as being drawn taut and, therefore, including a first suture end 124' and a second suture end 126', the first suture end 124' is passed through the first aperture 164' creating an entanglement loop 170a' at the first aperture 164' opposite the entry point for the first suture end 124' of the anchor suture loop 112'. The entanglement loop 170a' is then looped around the elongated body 162' adjacent the first end 120' of the anchor member 110' effectively locking the anchor suture loop 112' in position when tension is ultimately applied to engagement loop 172' formed by the anchor suture loop 112' between the first aperture 164' and the second aperture 166'. The second suture end 126' is then passed through the second aperture 166' creating an entanglement loop 170b' at the second aperture 166' opposite the entry point for the second suture end 126' of the anchor suture loop 112'. The entanglement loop 170b' is then looped around the elongated body 162' adjacent the second end 122' of the anchor member 110'. The application of tension effectively locks the anchor suture loop 112' in position when tension is ultimately applied to engagement loop 172' formed by the anchor suture loop 112 between the first aperture 164' and the second aperture 166', that is, the entanglement loops 170a', 170b' at the first and second ends 120', 122' of the anchor member 110' wrap thereabout in a manner gripping the anchor member 110'. It is appreciated as discussed below in accordance with an alternate embodiment that the anchor suture loop may also be provided as an adjustable loop with a sliding, locking knot and tensioning suture.

Figure 10A:
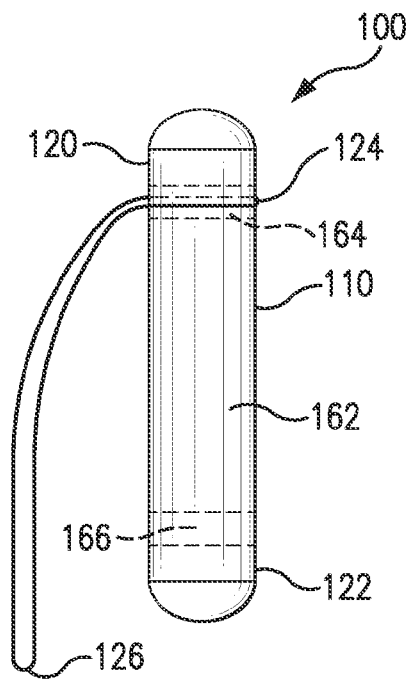
FIGS. 10A-C and 11A-D show alternate embodiments for securing an anchor suture loop to the anchor member shown in FIGS. 7, 8 and 9.
Figure 10B:
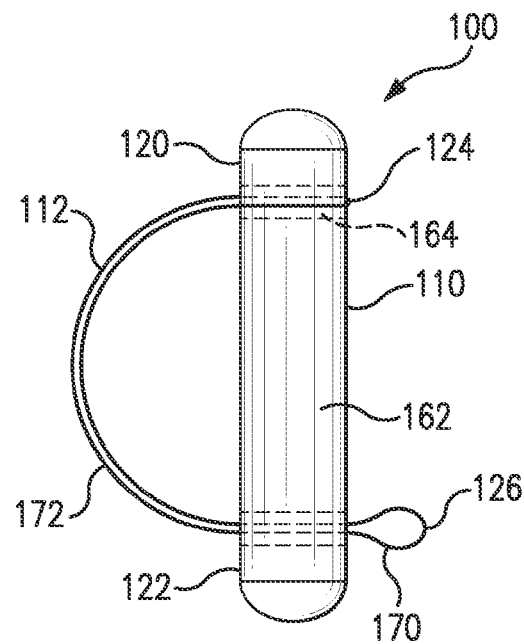
Figure 10C:
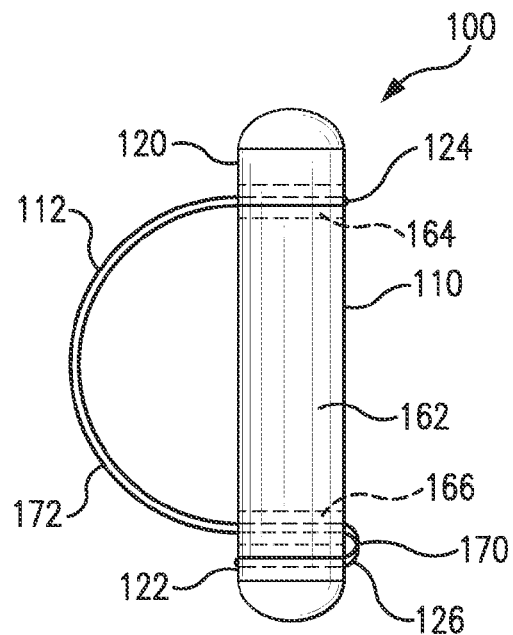
Figure 11A:
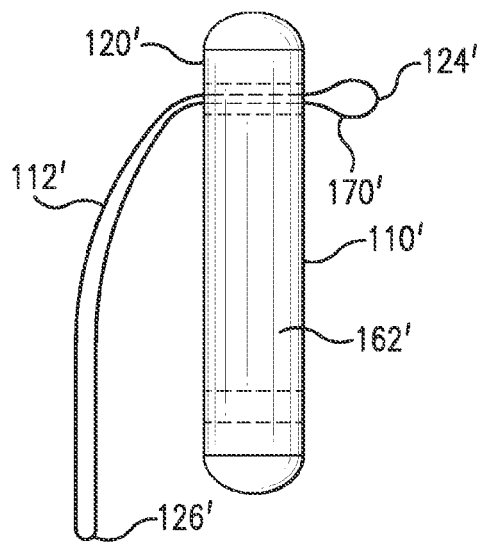
Figure 11B:
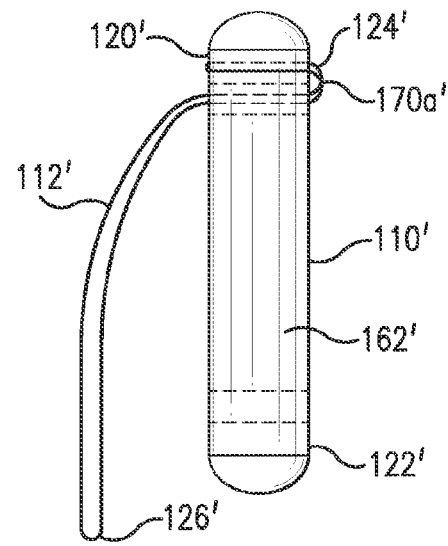
Figure 11C:
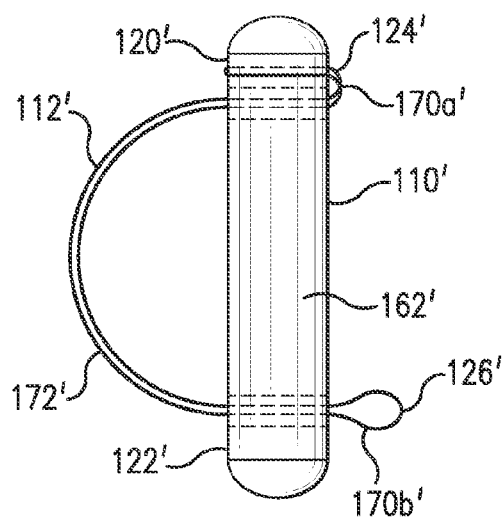
Figure 11D:
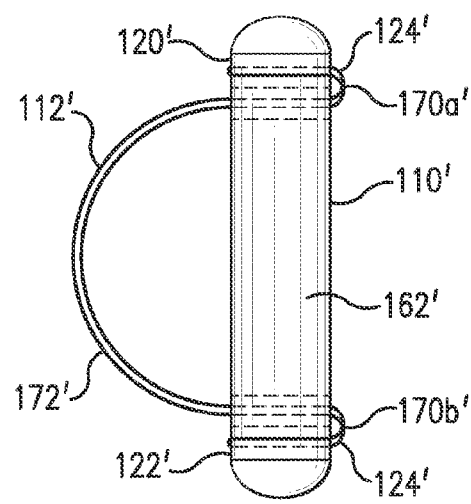
Figure 12:
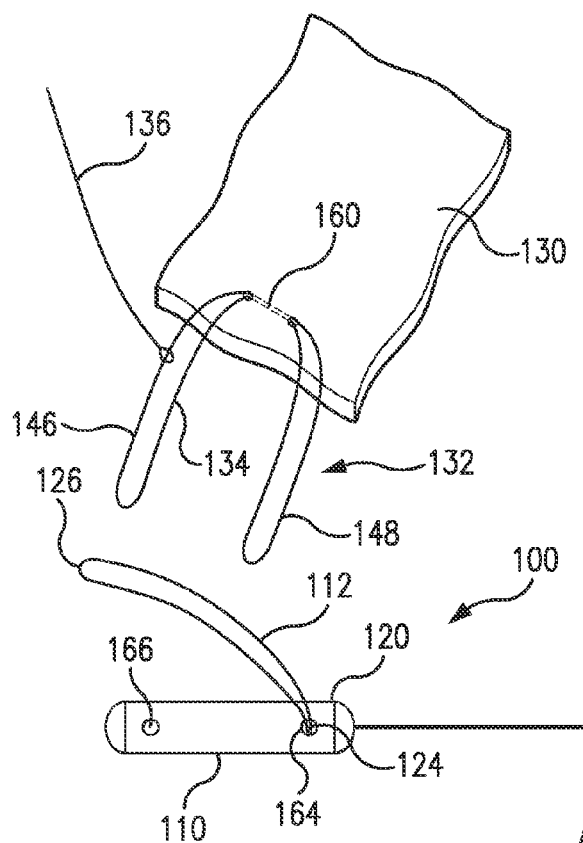
FIGS. 12, 13 and 14 show the steps of the present method as applied using the anchor member shown in FIGS. 7, 8 and 9.
Figure 13:
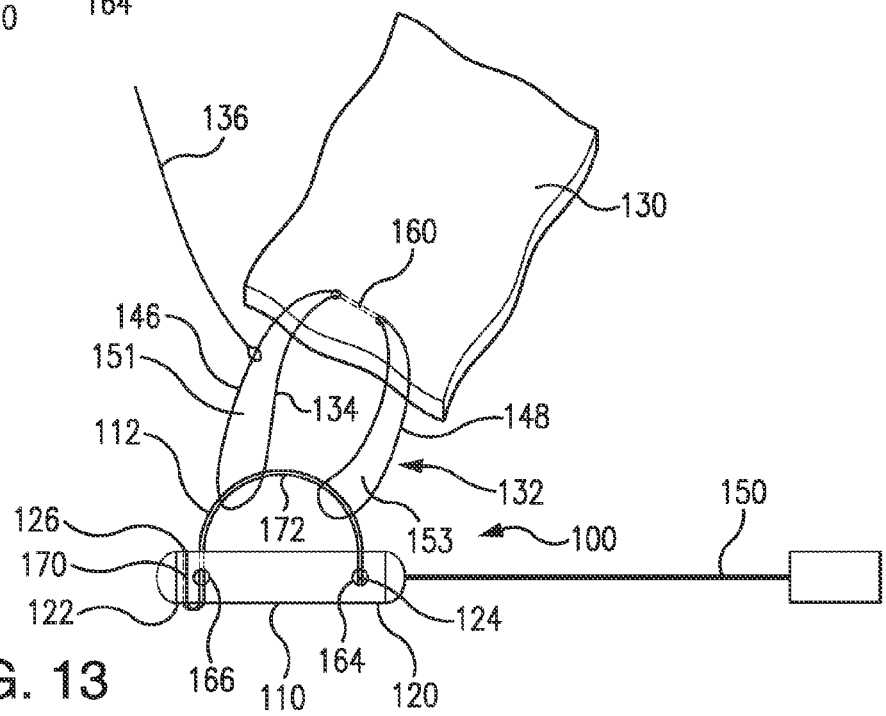
Figure 14:
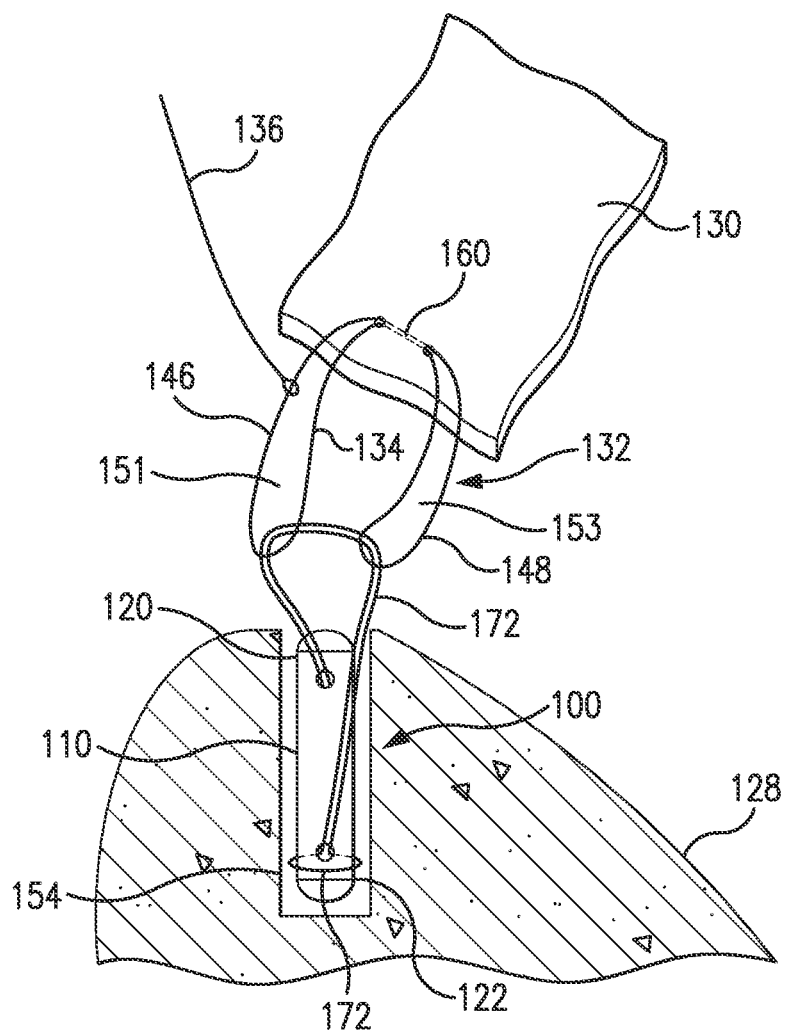
Figure 15:
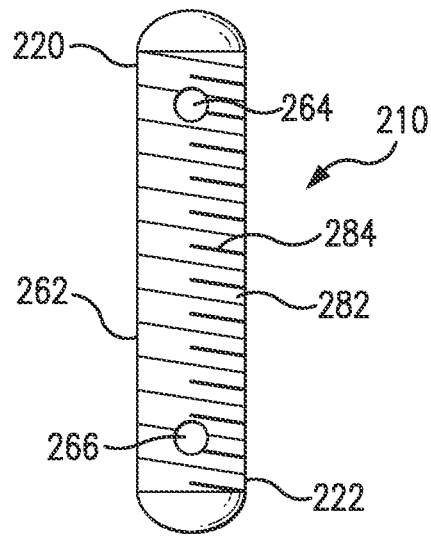
FIGS. 15, 16 and 17 are respectively a front plan view, a side plan view and a perspective view of an anchor member in accordance with yet another alternate embodiment.
Figure 16:
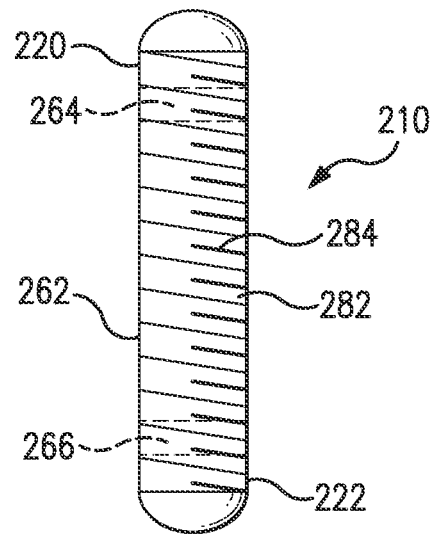
Figure 17:
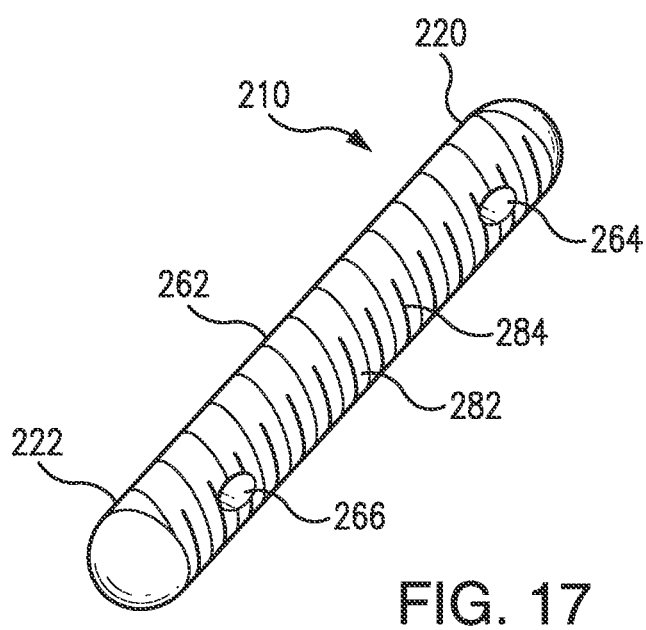

In accordance with the present method as applied in conjunction with the anchor suture loop attachment methodology described with reference to FIGS. 10A-C to (those skilled in the art would appreciate the utilization of the alternative anchor suture loop 112' attachment methodology described with reference to FIGS. 11A-11D would be the same with the exception of the attachment of the first suture end 124' of the anchor suture loop 112' to the first end 120' of the anchor member 110'), the adjustable suture loop 132 is first passed through the soft tissue 130 one wishes to secure to a bone mass 128. Referring to FIG. 12, the adjustable suture loop 132, in particular, the loop member 134 thereof is drawn through the soft tissue 130 with a surgical needle. The loop member 134 is passed through the soft tissue 130, one or more times, such that opposed first and second loop sections 146, 148 are formed when the loop member 134 is effectively split into two sections by the soft tissue 130; that is, with the soft tissue 130 between the opposed loop sections 146, 148. In particular, the loop member 134 is pulled through the soft tissue 130 until the two loop sections 146, 148 are of substantially the same size and in alignment. It is appreciated the loop member 34 is relatively long so that the opposed loop sections 146, 148 may be brought outside of the joint under repair. As shown in FIGS. 12, 13 and 14, the tensioning suture component 136 of the adjustable suture loop 132 also extends from one of the loop sections 146 and is similarly accessible from outside of the joint under repair.

With the loop sections 146, 148 of the adjustable suture loop 132 outside of joint, and with reference to FIG. 13, the anchor suture loop 112 of the anchor member 110 is entangled with the adjustable suture loop 132. In particular, the free end 124 of the anchor suture loop 112 is passed through the openings 151, 153 respectively defined by the opposed first and second loop sections 146, 148. That is, the free end 126 of the anchor suture loop 112 is drawn through the openings 151, 153 such that the anchor suture loop 112 is intertwined with the opposed loop section 146, 148. In this arrangement, the central portion 160 of the loop member 134 between the loop sections 146, 148 is in direct contact with the soft tissue 130 securing the anchor suture loop 112 to the soft tissue 130 such that the loop sections 146, 148 may simultaneously pull against the anchor suture loop 112 without fear that the loop member 134 will become disengaged with the soft tissue 130.

Thereafter, the free end 126 of the anchor suture loop 112 is captured by passing the free end 126 of the anchor suture loop 112 through the second aperture 166 creating an entanglement loop 170 at the second aperture 166 opposite the entry point for the free end 126 of the anchor suture loop 112, as well as an engagement loop 172 between the first aperture 164 and the second aperture 166. The entanglement loop 170 is then looped around the elongated body 162 adjacent the second end 122 of the anchor member 110 effectively locking the anchor suture loop 112 in position when tension is applied to engagement loop 172 formed by the anchor suture loop 112 between the first aperture 164 and the second aperture 166.

Ultimately, fixed attachment of the free end 126 of the anchor suture loop 112 at the second end 122 of the anchor member 110 is achieved upon deployment of the bone anchor 100 within the bone mass 128 to which the soft tissue 130 is secured. With the anchor suture loop 112 passed through the openings 151, 153 defined by the opposed first and second loop sections 146, 148 and the free end 126 of the anchor suture loop 112 secured at the second end 122 of the anchor member 110, the anchor suture loop 112 is tied to the loop member 134 and ultimately the soft tissue 130. Referring to FIG. 14, the bone anchor 100 is then inserted within an anchor hole 154 preferably predrilled in the bone mass 128 and the adjustable suture loop 132 is tightened as discussed above with regard to FIGS. 1 to 6.

In accordance with an alternate embodiment, as shown with reference to FIGS. 15-20, a bone screw 280 is used in conjunction with a bone anchor 200 for securely implanting of the bone anchor 200 within the bone mass 228. In particular, the bone anchor 200 is substantially the same as described above with reference to FIGS. 7-14, with the exception the external surface 282 of the anchor member 210 is provided with threading 284 shaped and dimensioned for engagement with threading 286 formed in an anchor recess 288 of the bone screw 280.

The bone anchor 200 is composed of an anchor member 210 having a first end 220 and a second end 222. A suture element 212, in the form of an anchor suture loop is provided and can be fixedly secured to the anchor member 210 as discussed below in greater detail.

The anchor member 210 includes an elongated body 262. The elongated body 262 is preferably cylindrical shaped and includes a rounded first end 220 and a rounded second end 222. The elongated body 262 includes spaced first and second apertures 264, 266. The first and second apertures 264, 266 are preferably positioned adjacent the first end 220 and the second end 222 of the elongated body 262, respectively.

The external surface 282 of the elongated body 262 is provided with threading 284 shaped and dimensioned for threaded engagement with a threaded anchor recess 288 formed in the bone screw 280. The anchor member 210 is also provided with a selectively detachable deployment arm 250 that is used in the manipulation of the anchor member 210 as it is deployed as discussed below in greater detail.

The anchor suture loop 212 is coupled to the anchor member 210 by controlled entanglement with the first and second apertures 264, 266 and the elongated body 262 of the anchor member 210 as discussed above with regard to FIGS. 10A-C and 11A-D. For the purposes of describing this embodiment, the coupling of the anchor suture loop 212 with the anchor member 210 is shown as described with reference to FIGS. 10A-C, although it is appreciated other attachment mechanisms (for example, as shown with reference to FIGS. 11A-D) may be employed.

Figure 18:
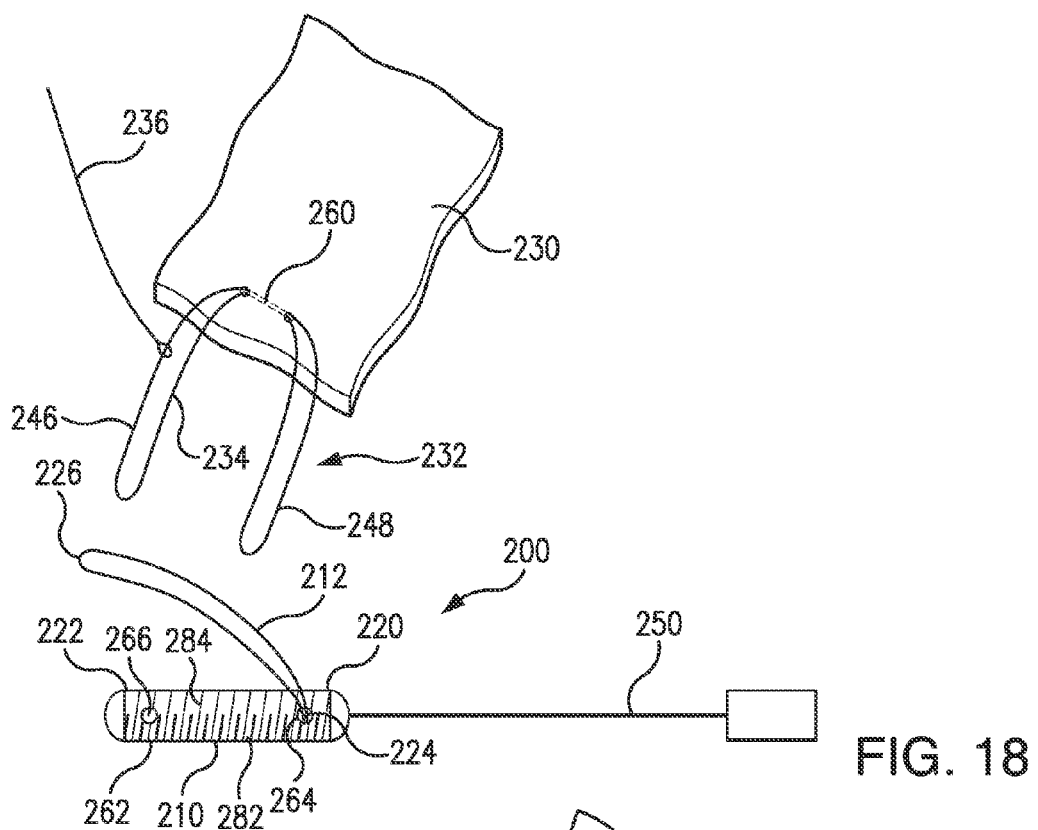
FIGS. 18, 19 and 20 show the steps of the present method as applied using the anchor member shown in FIGS. 15, 16 and 17.
Figure 19:
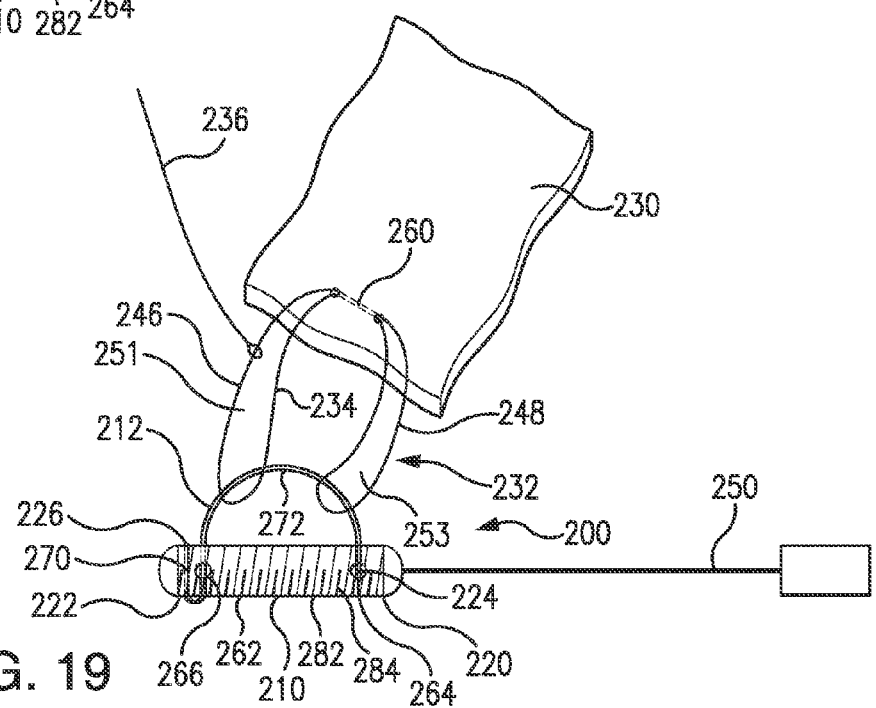
Figure 20:
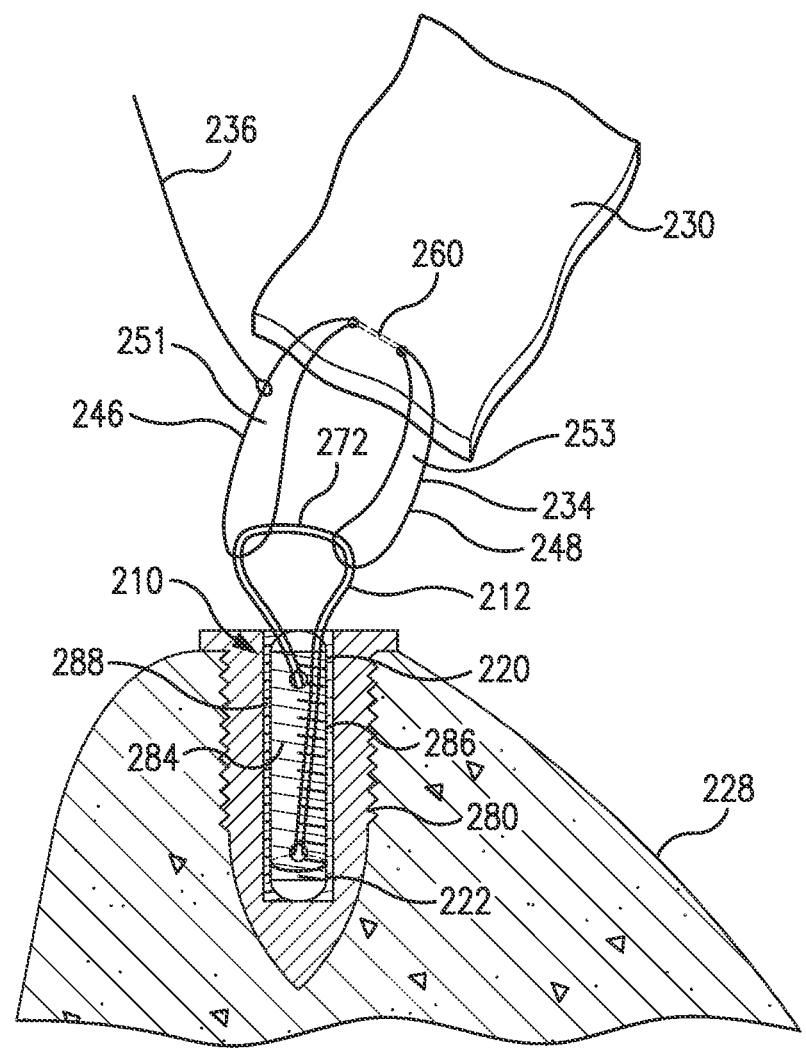

In accordance with the present method, the adjustable suture loop 232 is first passed through the soft tissue 230 one wishes to secure to a bone mass 228. Referring to FIG. 18, the adjustable suture loop 232, in particular, the loop member 234 thereof is drawn through the soft tissue 230 with a surgical needle. The loop member 234 is passed through the soft tissue 230, one or more times, such that opposed first and second loop sections 246, 248 are formed when the loop member 234 is effectively split into two sections by the soft tissue 230; that is, with the soft tissue 230 between the opposed loop sections 246, 248. In particular, the loop member 234 is pulled through the soft tissue 230 until the two loop sections 246, 248 are of substantially the same size and in alignment. It is appreciated the loop member 234 is relatively long so that opposed loop sections 246, 248 may be brought outside of the joint under repair. As shown in FIGS. 18, 19 and 20, the tensioning suture component 236 of the adjustable suture loop 232 also extends from the one of the loop sections 246 and is similarly accessible from outside of the joint under repair.

With the loop sections 246, 248 of the adjustable suture loop 232 outside of joint, and with reference to FIGS. 18 and 19, the anchor suture loop 212 of the anchor member 210 is entangled with the adjustable suture loop 232. In particular, the free end 226 of the anchor suture loop 212 is passed through the openings 251, 253 respectively defined by the opposed first and second loop sections 246, 248. That is, the free end 226 of the anchor suture loop 212 is drawn through the openings 251, 253 such that the anchor suture loop 212 is intertwined with the opposed loop sections 246, 248. In this arrangement, the central portion 260 of the loop member 234 between the loop sections 246, 248 is in direct contact with the soft tissue 230 securing the anchor suture loop 212 to the soft tissue 230 such that the loop sections 246, 248 may simultaneously pull against the anchor suture loop 212 without fear that the loop member 234 will become disengaged with the soft tissue 230.

Thereafter, the free end 226 of the anchor suture loop 212 is captured by passing the free end 226 of the anchor suture loop 212 through the second aperture 266 creating an entanglement loop 270 at the second aperture 266 opposite the entry point for the free end 226 of the anchor suture loop 212, as well as an engagement loop 272 between the first aperture 264 and the second aperture 266. The entanglement loop 270 is then looped around the elongated body 262 adjacent the second end 222 of the anchor member 210 effectively locking the anchor suture loop 212 in position when tension is applied to engagement loop 272 formed by the anchor suture loop 212 between the first aperture 264 and the second aperture 266.

Ultimately, fixed attachment of the free end 226 of the anchor suture loop 212 at the second end 222 of the anchor member 210 is achieved upon deployment of the bone anchor 200 within the bone screw 280, and ultimately the bone mass 228, to which the soft tissue 230 is secured. With the anchor suture loop 212 passed through the openings 251, 253 defined by the opposed first and second loop sections 246, 248 and the free end 226 of the anchor suture loop 212 secured at the second end 222 of the anchor member 210, the anchor suture loop 212 is tied to the loop member 234 and ultimately the soft tissue 230. Referring to FIG. 20, the bone anchor 200 is then inserted within the threaded anchor recess 288 formed in the bone screw 280 previously applied to the bone mass 228 and the adjustable suture loop 232 is tightened as discussed above with regard to FIGS. 1 to 6. It is appreciated as discussed below in accordance with an alternate embodiment that the anchor suture loop may also be provided as an adjustable loop with a sliding, locking knot and tensioning suture.

Figure 21:
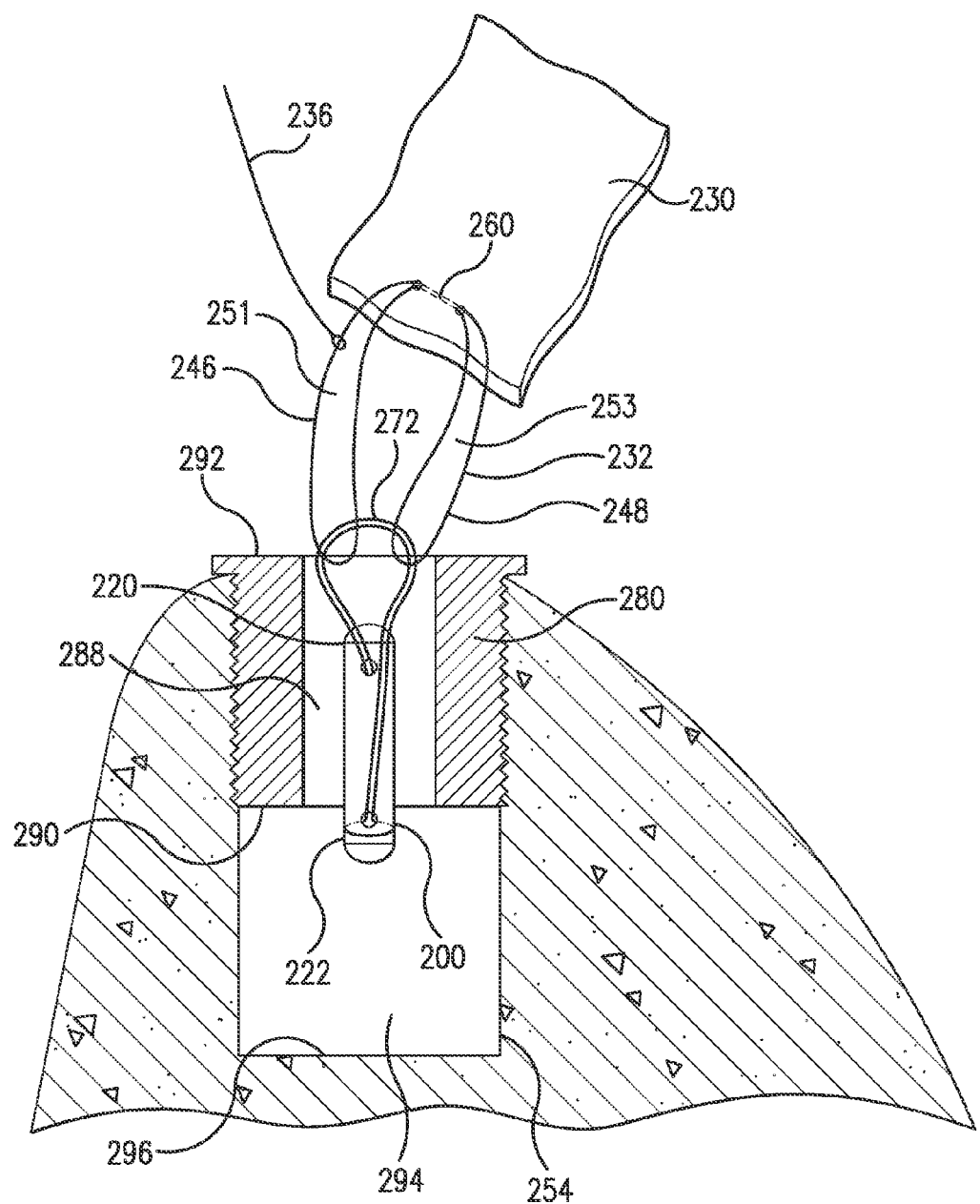
FIGS. 21 and 22 disclose an alternate embodiment in accordance with the present invention.
Figure 22:
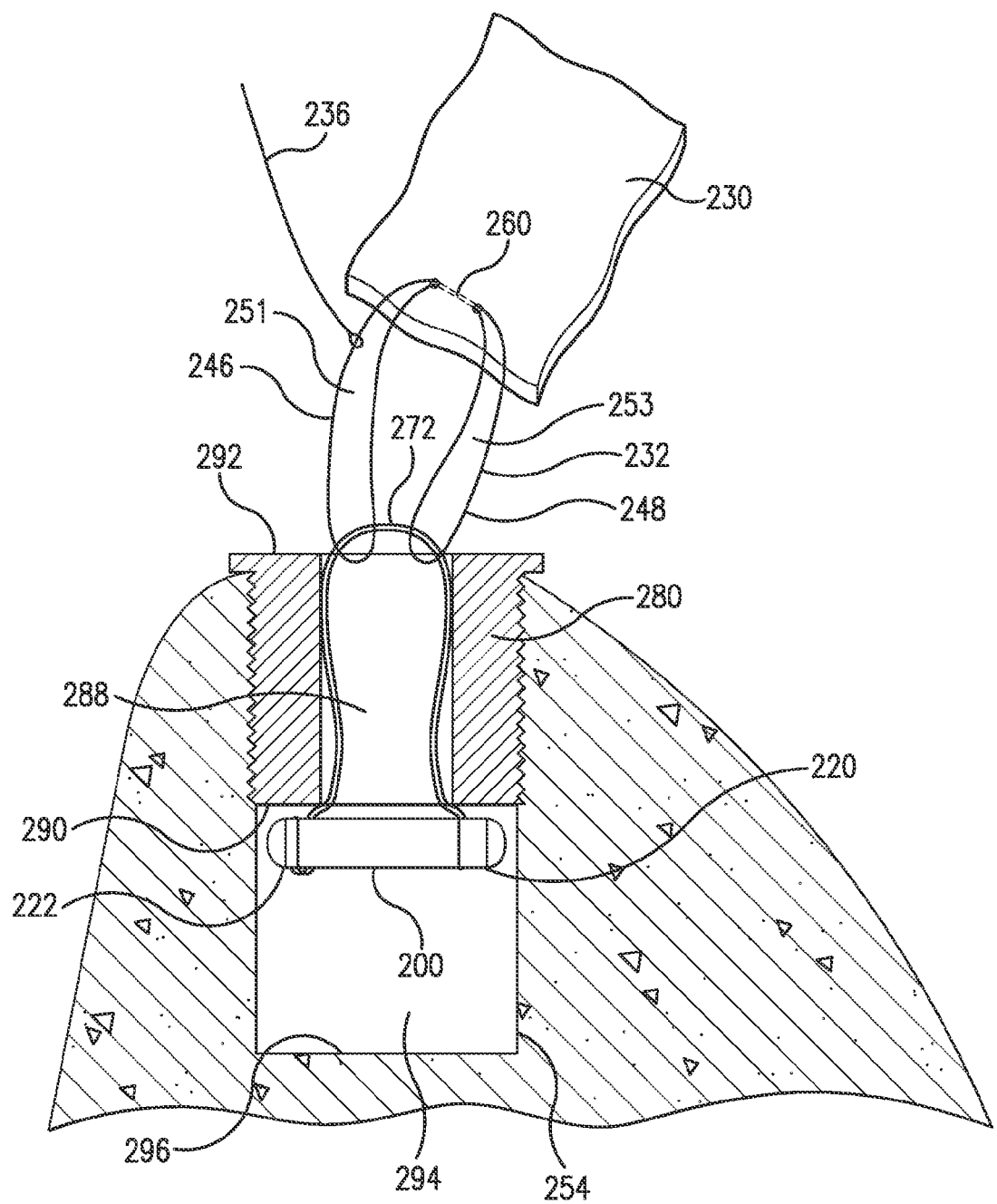

With reference to FIGS. 21 and 22, an alternate embodiment is disclosed that is similar to that disclosed with reference to FIGS. 15-20. In the alternate embodiment, the distal end 290 of the cylindrical anchor mounting sleeve or bone screw 280 is open, allowing access to the internal bone mass; that is, the bone screw 280 is in the form of an open cylindrical anchor mounting sleeve with or without external threading. Any fixation method can be utilized to affix the anchor mounting sleeve to the bone mass. It is appreciated the open cylindrical anchor mounting sleeve provides an anchor recess (or anchor passageway 288 in accordance with such an embodiment) extending from the proximal end 292 of the open cylindrical anchor mounting sleeve 280 to the distal end 290 of the open cylindrical anchor mounting sleeve 280. As will be explained below, the bone anchor is secured in a different manner, to effectuate tissue repair, from that disclosed above and threading on the bone anchor is therefore not necessary. As such, reference numerals used in conjunction with FIGS. 15-20 have also been used, where possible, based upon the similarity of the two embodiments.

The anchor passageway 288, in the open cylindrical anchor mounting sleeve 280, allows for capture of the bone anchor 200 on the distal end 290 of the open cylindrical anchor mounting sleeve 280 within a small cavity 294 defined by the bottom 296 of the anchor hole 254 and the distal end 290 of the open cylindrical anchor mounting sleeve 280. The bone anchor 200 is passed through the anchor passageway 288 with the longitudinal axis of the bone anchor 200 aligned substantially parallel with the longitudinal axis of the open cylindrical anchor mounting sleeve 280 (see FIG. 21). Once the bone anchor 200 has passed fully through the anchor passageway 288 and into the small cavity 294 defined by the bottom 296 of the anchor hole 254 and the distal end 290 of the open cylindrical anchor mounting sleeve 280, the bone anchor 200 may be oriented to extend transversely to the longitudinal axis of the open cylindrical anchor mounting sleeve 280 and thereby lock the bone anchor 200 in position due to the fact the length of the bone anchor 200 is greater than the diameter of the anchor passageway 288 or alternatively, the bone anchor 200 is shaped in such a manner, for example, a wedge-shaped suture anchor, such as those sold by Mitek Surgical Products, Inc. and depicted in U.S. Pat. No. 5,683,418, and having an edge shaped in such a manner to capture the distal end of the open cylindrical anchor mounting sleeve 280 (see FIG. 22). It is also appreciated, the internal structure of the bone mass is not very dense and the bone anchor 200 may actually be pushed into, and manipulated within the bone mass for orientation as shown in FIG. 22, thereby obviating the need for a deep hole or a hole extending below the distal end of the open cylindrical anchor mounting sleeve 280.

As with the embodiment disclosed with reference to FIGS. 15-20, once the bone anchor 200 is locked in position within the small cavity 294, the adjustable suture loop 232 may be tightened as discussed above with regard to FIGS. 1 to 6.

In accordance with yet another embodiment of the present invention, and with reference to FIGS. 23-26, an alternate method and apparatus is disclosed wherein first and second bone anchors 300a, 300b are used in securing of tissue. As with the embodiment of FIGS. 21 and 22, the distal end 390 of the cylindrical anchor mounting sleeve or bone screw 380 is open, allowing access to the internal bone mass; that is, the bone screw 380 is in the form of an open cylindrical anchor mounting sleeve with or without external threading. Any fixation method can be utilized to affix the anchor mounting sleeve to the bone mass. The open cylindrical anchor mounting sleeve 380 provides an anchor passageway 388 extending from the proximal end 392 of the open cylindrical anchor mounting sleeve 380 to the distal end 390 of the open cylindrical anchor mounting sleeve 380.

Figure 26:
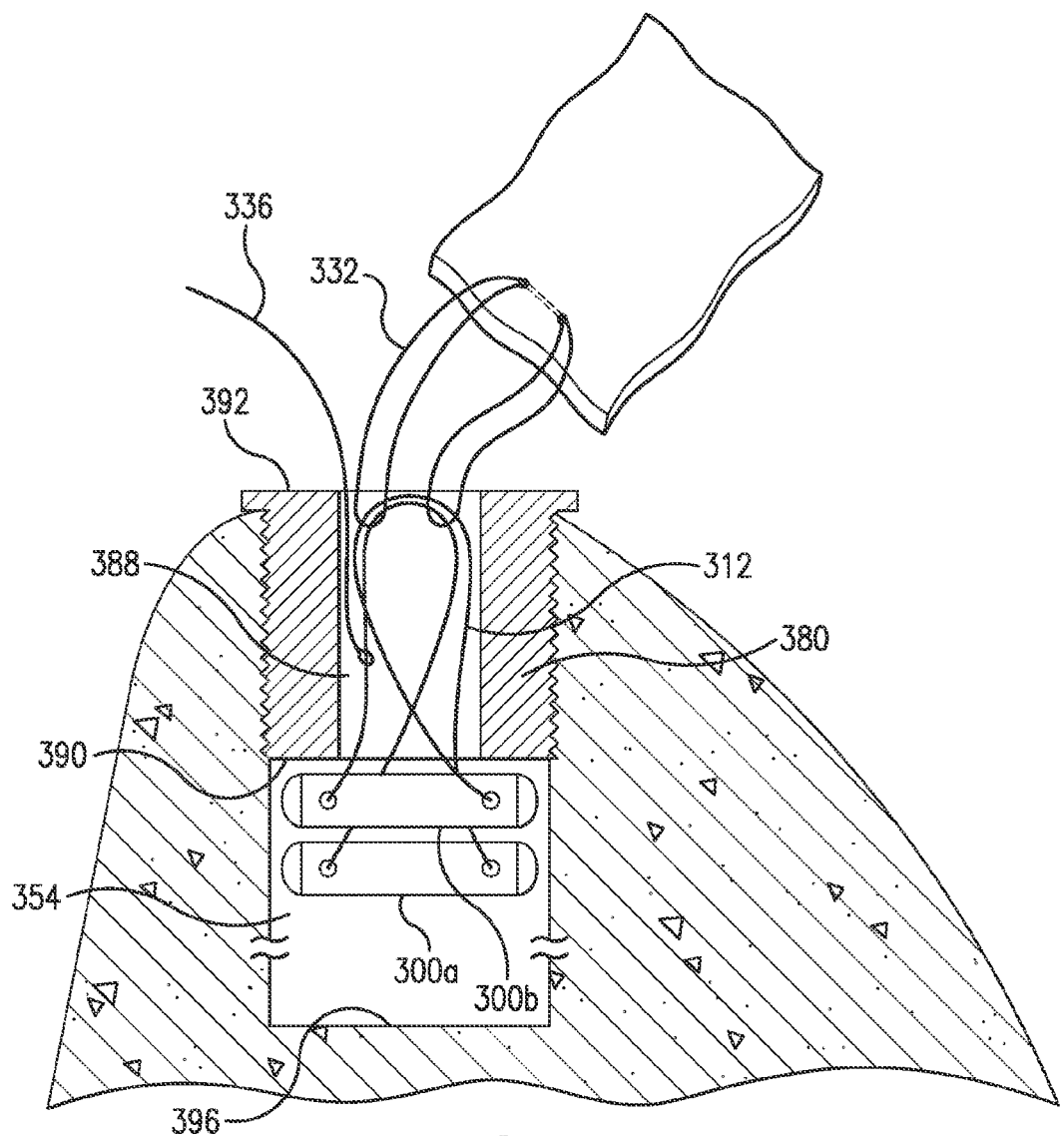

The anchor passageway 388, in the open cylindrical anchor mounting sleeve 380, allows for capture of the bone anchors 300a, 300b on the distal end 390 of the open cylindrical anchor mounting sleeve 380 within a small cavity 394 defined by the bottom 396 of the anchor hole 354 and the distal end 390 of the open cylindrical anchor mounting sleeve 380. The bone anchors 300a, 300b are passed through the anchor passageway 388 with the longitudinal axis of the bone anchors 300a, 300b aligned substantially parallel with the longitudinal axis of the open cylindrical anchor mounting sleeve 380 (see FIG. 24 where the first bone anchor 300a is being passed through the mounting sleeve). Once each of the bone anchors 300a, 300b have passed fully through the anchor passageway 388 and into the small cavity 394 defined by the bottom 396 of the anchor hole 354 and the distal end 390 of the open cylindrical anchor mounting sleeve 380, the bone anchors 300a, 300b are oriented to extend transversely to the longitudinal axis of the open cylindrical anchor mounting sleeve 380 and thereby lock the bone anchors 300a, 300b in position due to the fact the length of the bone anchors 300a, 300b is greater than the diameter of the anchor passageway 388. It is also appreciated, the internal structure of the bone mass is not very dense and the bone anchors 300a, 300b may actually be pushed into, and manipulated within the bone mass for orientation as shown in FIG. 26, thereby obviating the need for a deep hole or a hole extending below the distal end 390 of the open cylindrical anchor mounting sleeve 380.

More particularly, each of the first and second bone anchors 300a, 300b is composed of an anchor member 310 having a first end 320 and a second end 322. A suture element 312, in the form of an anchor suture loop as discussed above, is provided and is fixedly secured to the anchor member 310 as discussed below in greater detail.

The anchor member 310 includes an elongated body (or member) 362. The elongated body 362 is preferably cylindrical shaped and includes a rounded first end 320 and a rounded second end 322. The anchor suture loop 312 is coupled to the anchor members 310 by securing opposite ends thereof to the respective first and second bone anchor 300*a*, 300*b*. Several methods for attachment are contemplated in accordance with the present invention. For example, fixed & adjustable loops are contemplated, as is a sliding, locking knot as described above. It is also appreciated, the elongated bodies of the anchor members need not be connected by a loop, but could be connected by a suture strand or multiple suture loops.

In contrast to the prior embodiments, and as discussed below in greater detail, the sliding, locking knot 338 is formed on the anchor suture loop 312 allowing for adjustability thereof. As such, the anchor suture loop 312 is provided with a tensioning suture component 336 similar to that disclosed with reference to the adjustable suture loop disclosed above. However, it is appreciated; the concepts underlying this embodiment could also be achieved with the sliding, locking knot being formed on the adjustable suture loop as discussed above. As such, what is referred to above as the adjustable suture loop is referenced below as the tissue suture loop.

Figure 23:
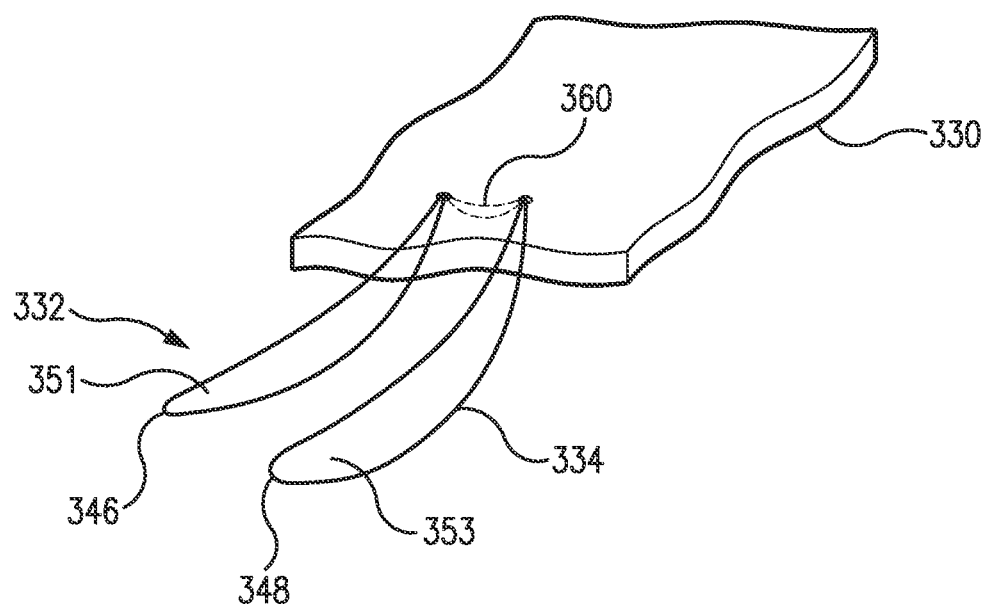
FIGS. 23, 24, 25 and 26 show an alternate system associated methodology in accordance with the present invention.

In accordance with the present method, the tissue suture loop 332 is first passed through the soft tissue 330 one wishes to secure to a bone mass 328. Referring to FIG. 23, the tissue suture loop 332, in particular, the loop member 334 thereof, is drawn through the soft tissue 330 with a surgical needle (or a "utility suture" as discussed above). The loop member 334 is passed through the soft tissue 330, one or more times, such that opposed first and second loop sections 346, 348 are formed when the loop member 334 is effectively split into two sections by the soft tissue 330; that is, with the soft tissue 330 between the opposed loop sections 346, 348. In particular, the loop member 334 is pulled through the soft tissue 330 until the two loop sections 346, 348 are of substantially the same size and in alignment. It is appreciated the loop member 334 is relatively long so that opposed loop sections 346, 348 may be brought outside of the joint under repair. Although the tensioning suture component forms part of the anchor suture loop in accordance with a preferred embodiment of the methodology and system disclosed in FIGS. 23-26, it is appreciated the tissue suture loop may be formed with a tensioning suture component as discussed above with the prior embodiments. In such situations, the length of the loop member of the tissue suture loop is relevant. However, where the anchor suture loop is adjustable, the loop member of the tissue suture loop may be a small, fixed size loop.

Figure 24:
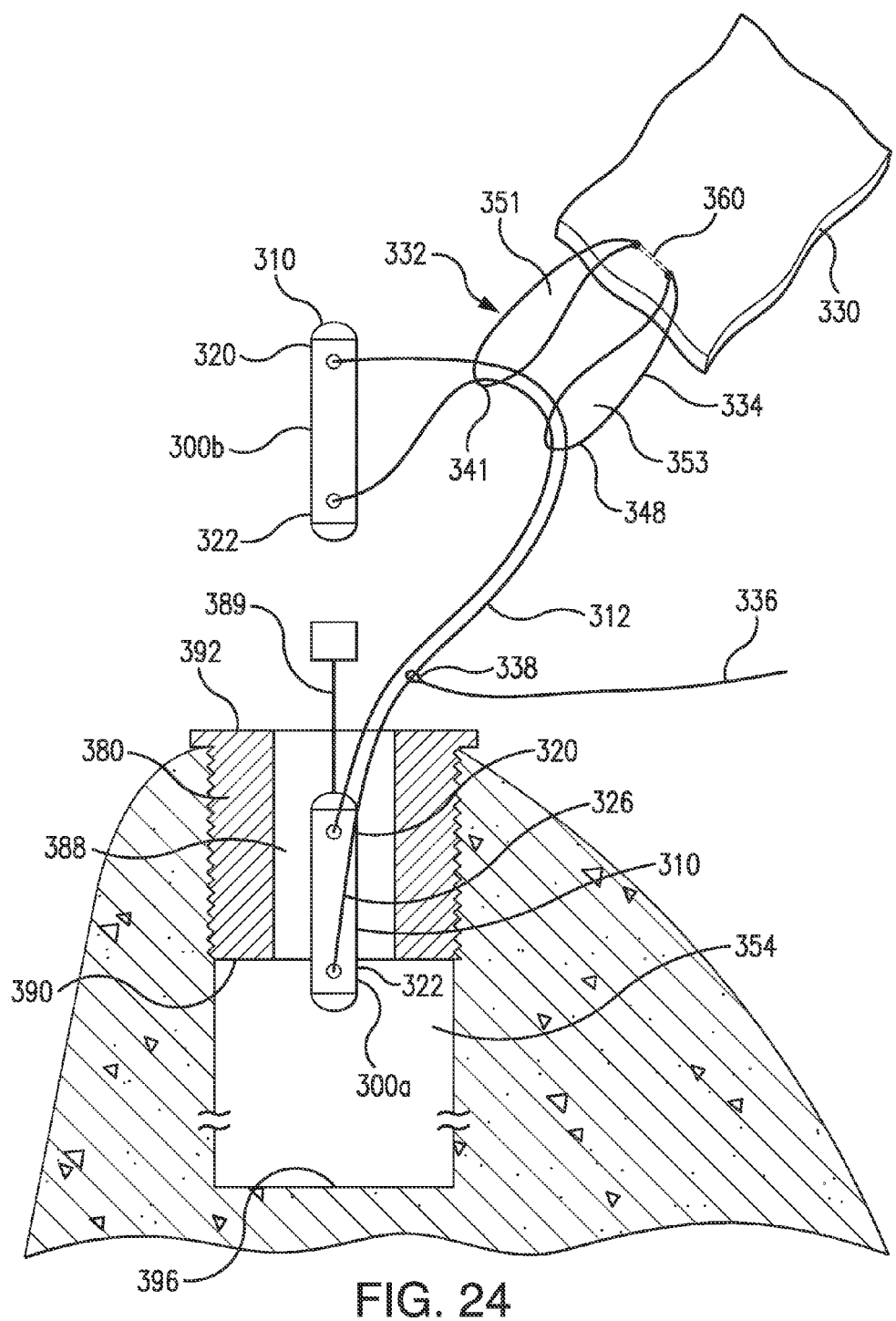
Figure 25:
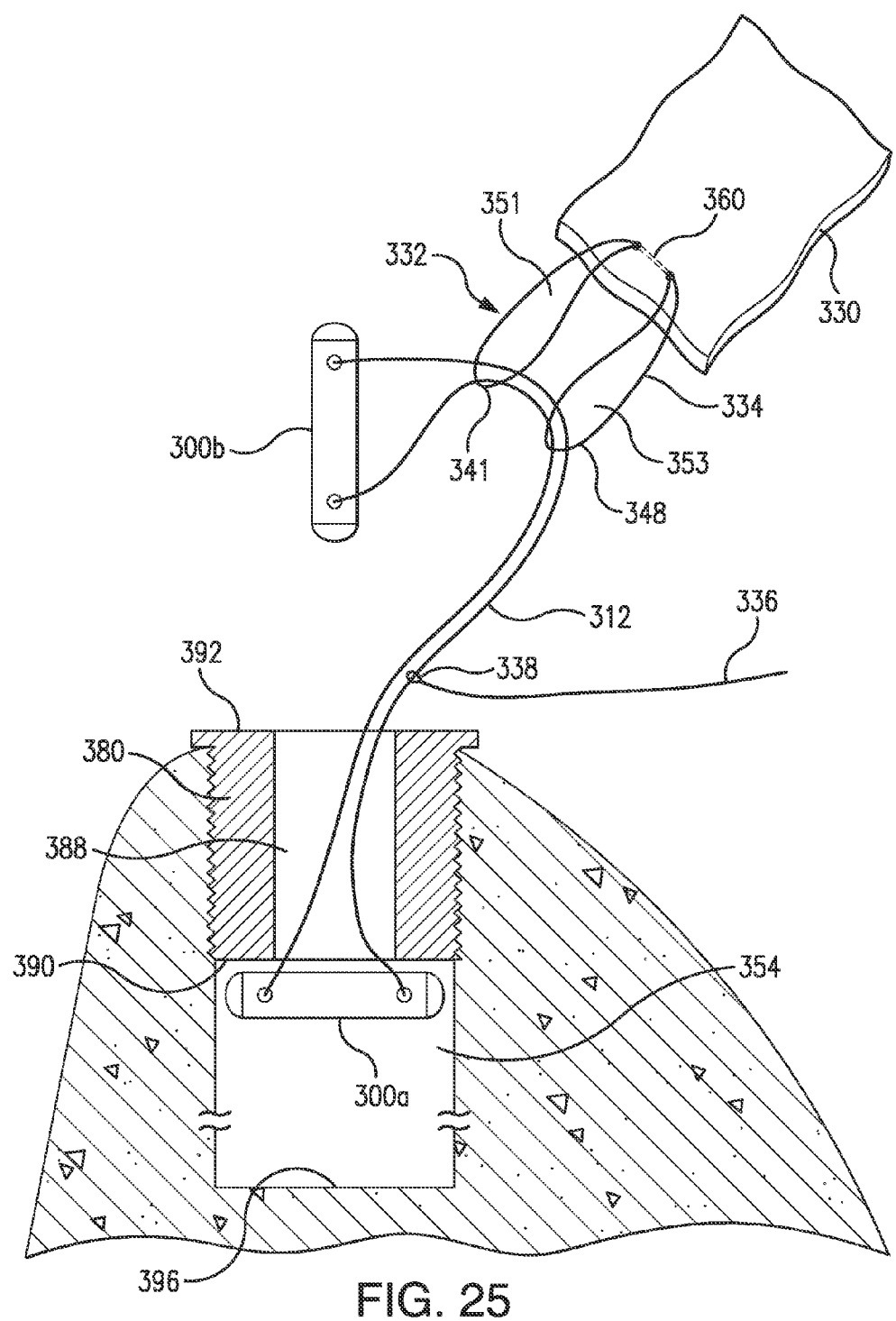

With the loop sections 346, 348 of the adjustable suture loop 332 outside of joint, and with reference to FIGS. 24, 25 and 26, the anchor suture loop 312 of the anchor member 310 is entangled with the adjustable suture loop 332. In particular, the first end 326 of the anchor suture loop 312 to which the first bone anchor 300*a* is secured, is passed through the anchor passageway 388 under the control of a delivery device 389 with the longitudinal axis of the first bone anchor 300*a* aligned substantially parallel with the longitudinal axis of the open cylindrical anchor mounting sleeve 380 (see FIG. 24). Once the first bone anchor 300*a* has passed fully through the anchor passageway 388 and into the small cavity 394 defined by the bottom 396 of the anchor hole 354 and the distal end 390 of the open cylindrical anchor mounting sleeve 380, the first bone anchor 300*a* is oriented to extend transversely to the longitudinal axis of the open cylindrical anchor mounting sleeve 380 and thereby lock the first bone anchor 300*a* in position due to the fact the length of the first bone anchor 300*a* is greater than the diameter of the anchor passageway 388 (see FIG. 25). As mentioned above It is also appreciated, the internal structure of the bone mass is not very dense and the first bone anchor 300*a* may actually be pushed into, and manipulated within the bone mass for orientation thereby obviating the need for a deep hole or a hole extending below the distal end of the open cylindrical anchor mounting sleeve 380.

Referring now to FIG. 25, with the first bone anchor 300*a* secured to the cylindrical anchor mounting sleeve 380, the second bone anchor 300*b* and the second end of the anchor suture loop 312 are passed through the openings 351, 353 respectively defined by the opposed first and second loop sections 346, 348. That is, the second end 326 of the anchor suture loop 312 is drawn through the openings 351, 353 such that the anchor suture loop 312 is intertwined with the opposed loop sections 346, 348. In this arrangement, the central portion 360 of the loop member 334 between the loop sections 346, 348 is in direct contact with the soft tissue 330 securing the anchor suture loop 312 to the soft tissue 330 such that the loop sections 346, 348 may simultaneously pull against the anchor suture loop 312 without fear that the loop member 334 will become disengaged with the soft tissue 330. Thereafter, and with reference to FIG. 26, the second bone anchor 300*b* is captured within the cylindrical anchor mounting sleeve 380 by passing it through the cylindrical anchor mounting sleeve 280 in the same manner as the first bone anchor 300*a*. That is, and as with the first bone anchor 300*a*, the second bone anchor 300*b* is passed through the anchor passageway 388 with the longitudinal axis of the bone anchor 300*b* aligned substantially parallel with the longitudinal axis of the open cylindrical anchor mounting sleeve 380. Once the bone anchor 300 has passed fully through the anchor passageway 388 and into the small cavity 394 defined by the bottom 396 of the anchor hole 354 and the distal end 390 of the open cylindrical anchor mounting sleeve 380, the bone anchor 300*b* is oriented to extend transversely to the longitudinal axis of the open cylindrical anchor mounting sleeve 380 and thereby lock the second bone anchor 300*b* in position due to the fact the length of the bone anchor 300*b* is greater than the diameter of the anchor passageway 388. As mentioned above It is also appreciated, the internal structure of the bone mass is not very dense and the bone anchor 300*b* may actually be pushed into, and manipulated within the bone mass for orientation above the first bone anchor as shown in FIG. 22.

With the anchor suture loop 312 passed through the openings 351, 353 defined by the opposed first and second loop sections 346, 348 and the free end 326 of the anchor suture loop 312 secured at the second end 322 of the anchor member 310, the anchor suture loop 312 is tied, linked or entangled to the loop member 334 and ultimately the soft tissue 330. The anchor suture loop 312 may then be is tightened by pulling upon tensioning suture component 336 as discussed above with regard to FIGS. 1 to 6. It is appreciated that this embodiment may employ a sliding, locking knot on the anchor suture loop to facilitating tightening as discussed above.

In many situations throughout the discussion above, the terminology relating to the secure attachment of soft tissue to bone mass has been used. Such terminology refers to the attachment or reattachment of tissue to a bone mass by securely binding the tissue to the bone mass utilizing the novel knotless suture anchor assembly. The suture element can be made up of a known suture material, or it can be made of polymer materials, or can be formed of bioabsorbable/biocomposite material such as a polylactide polymer.

While the preferred embodiments have been shown and described, it will be understood that there is no intent to limit the invention by such disclosure, but rather, is intended to cover all modifications and alternate constructions falling within the spirit and scope of the invention.

The invention claimed is:

1. A suture anchoring system, comprising:
   a mounting sleeve having an open distal end and an open proximal end defining a passageway therethrough;
   an elongated cylindrical member having a first end and a second end, the first end including a first aperture and the second end including a second aperture, and an anchor suture having a first end and a second end with the first end of the anchor suture fixedly secured to the first aperture of the elongated cylindrical member;
   a separate non interlocked tissue suture loop, wherein the separate non interlocked tissue suture loop includes a one-way sliding, locking knot with a tensioning suture component extending from the one-way sliding, locking knot; and
   wherein tissue is configured to be secured to a bone mass by passing the separate non interlocked tissue suture loop through the tissue such that opposed first and second loop sections are formed, passing the second end of the anchor suture through first and second openings respectively defined by the opposed first and second loop sections, capturing the second end of the anchor suture after passing through the first and second openings in the second aperture of the second end of the elongated cylindrical member, and then securing the elongated cylindrical member to the mounting sleeve in an anchor hole that is configured to be in the bone mass.

2. The suture anchoring system according to claim 1, wherein the anchor suture is an anchor suture loop and includes a one-way sliding, locking knot with a tensioning suture component extending therefrom.

3. The suture anchoring system according to claim 1, wherein the elongated cylindrical member with the anchor suture secured to the first end and the second end of the elongated cylindrical member and passed through the separate non interlocked tissue suture loop, engage with a recess of the mounting sleeve.

4. The suture anchoring system according to claim 1, wherein the anchor suture includes a one-way sliding, locking knot with a tensioning suture component extending therefrom.

5. A suture anchoring system, comprising:
   a mounting sleeve having an open distal end and an open proximal end defining a passageway therethrough;
   a first elongated cylindrical member having a first end and a second end, the first end including a first aperture and the second end including a second aperture, and an anchor suture having a first end and a second end with a first end of the anchor suture fixedly secured to the first aperture and second aperture of the first cylindrical elongated member;
   a second elongated cylindrical member having a first end and a second end, the first end including a first aperture and the second end including a second aperture with the second end of the anchor suture fixedly secured to the first aperture and second aperture of the second elongated cylindrical member;
   a separate non interlocked tissue suture loop, wherein the separate non interlocked tissue suture loop includes a one-way sliding, locking knot with a tensioning suture component extending from the one-way sliding, locking knot; and
   wherein tissue is configured to be secured to a bone mass by passing the separate non interlocked tissue suture loop through the tissue such that opposed first and second loop sections are formed, passing the second elongated cylindrical member with the second end of the anchor suture through first and second openings respectively defined by the opposed first and second loop sections and then securing the first elongated cylindrical member and the second elongated cylindrical member to the mounting sleeve in an anchor hole that is configured to be in the bone mass.

6. The suture anchoring system according to claim 5, wherein the anchor suture loop includes a one-way sliding, locking knot with a tensioning suture component extending therefrom.

* * * * *